United States Patent
Castillo (10) Patent No.: US 9,277,971 B2
(45) Date of Patent: *Mar. 8, 2016

(54) LITHIUM SILICATE GLASS CERAMIC FOR FABRICATION OF DENTAL APPLIANCES

(71) Applicant: James R. Glidewell Dental Ceramics, Inc., Newport Beach, CA (US)

(72) Inventor: Rodolfo Castillo, Boca Raton, FL (US)

(73) Assignee: James R. Glidewell Dental Ceramics, Inc.

(*) Notice: Subject to any disclaimer, the term of this patent is extended or adjusted under 35 U.S.C. 154(b) by 0 days.

This patent is subject to a terminal disclaimer.

(21) Appl. No.: 13/685,450

(22) Filed: Nov. 26, 2012

(65) Prior Publication Data

US 2014/0148328 A1 May 29, 2014
US 2015/0245885 A9 Sep. 3, 2015

Related U.S. Application Data

(63) Continuation-in-part of application No. 13/374,040, filed on Dec. 8, 2011, which is a continuation-in-part of application No. 12/592,825, filed on Dec. 3, 2009, now abandoned, which is a continuation-in-part of application No. 12/283,472, filed on Sep. 12, 2008, now Pat. No. 7,892,995, which is a continuation-in-part of application No. 12/082,576, filed on Apr. 11, 2008, now abandoned.

(51) Int. Cl.
- *C03C 10/04* (2006.01)
- *A61C 5/10* (2006.01)
- *C03C 10/00* (2006.01)
- *A61C 13/00* (2006.01)
- *A61K 6/027* (2006.01)

(52) U.S. Cl.
CPC ............. *A61C 5/10* (2013.01); *A61C 13/0022* (2013.01); *A61K 6/0273* (2013.01); *C03C 10/00* (2013.01); *C03C 10/009* (2013.01); *C03C 10/0027* (2013.01)

(58) Field of Classification Search
CPC ............. A61K 6/0273; C03C 10/0009; C03C 10/0027
USPC ................................. 501/5; 106/35
See application file for complete search history.

(56) References Cited

U.S. PATENT DOCUMENTS

| 3,006,775 A * | 10/1961 | Chen ................................. 501/7 |
| 4,189,325 A | 2/1980 | Barrett et al. |
| 4,205,982 A | 6/1980 | German |
| 4,480,044 A | 10/1984 | McAlinn |
| 4,515,634 A | 5/1985 | Wu et al. |
| 4,992,297 A | 2/1991 | Van der Zel |
| 5,219,799 A | 6/1993 | Beall et al. |
| 5,290,371 A | 3/1994 | Cameron et al. |
| 5,698,019 A | 12/1997 | Frank et al. |
| 5,744,208 A | 4/1998 | Beall et al. |
| 5,968,856 A | 10/1999 | Schweiger et al. |
| 6,342,458 B1 | 1/2002 | Schweiger et al. |
| 6,455,451 B1 | 9/2002 | Brodkin et al. |
| 6,514,893 B1 | 2/2003 | Schweiger et al. |
| 6,517,623 B1 | 2/2003 | Brodkin et al. |
| 6,606,884 B2 | 8/2003 | Schweiger et al. |
| 6,802,894 B2 | 10/2004 | Brodkin et al. |
| 6,818,573 B2 | 11/2004 | Petticrew |
| 7,316,740 B2 | 1/2008 | Schweiger et al. |
| 7,381,258 B2 | 6/2008 | Krumbholz |
| 7,452,836 B2 | 11/2008 | Apel et al. |
| 7,816,291 B2 | 10/2010 | Schweiger et al. |
| 7,867,930 B2 | 1/2011 | Apel et al. |
| 7,867,931 B2 | 1/2011 | Apel et al. |
| 7,871,948 B2 | 1/2011 | Apel et al. |
| 7,892,995 B2 | 2/2011 | Castillo |
| 8,042,358 B2 | 10/2011 | Schweiger et al. |
| 8,047,021 B2 | 11/2011 | Schweiger et al. |
| 2002/0198093 A1 | 12/2002 | Van der Zel |
| 2004/0197738 A1 | 10/2004 | Ban et al. |
| 2005/0155518 A1 | 7/2005 | Krumbholz |
| 2005/0288165 A1 | 12/2005 | Krumbholz |
| 2006/0194895 A1 | 8/2006 | Loveridge et al. |
| 2009/0256274 A1 * | 10/2009 | Castillo .......................... 264/16 |
| 2009/0258778 A1 | 10/2009 | Castillo |
| 2009/0291820 A1 | 11/2009 | Schweiger et al. |
| 2010/0083706 A1 | 4/2010 | Castillo |
| 2011/0009254 A1 | 1/2011 | Schweiger et al. |
| 2011/0256409 A1 | 10/2011 | Ritzberger et al. |
| 2012/0094822 A1 | 4/2012 | Castillo |
| 2012/0148988 A1 | 6/2012 | Castillo et al. |

FOREIGN PATENT DOCUMENTS

| EP | 2664594 | * 11/2013 |
| WO | WO 2011/076422 | 6/2011 |
| WO | WO 2012/059143 | 5/2012 |

OTHER PUBLICATIONS

PCT International Search Report in PCT/US2013/024692 dated Apr. 15, 2013.

* cited by examiner

Primary Examiner — Karl Group (57) ABSTRACT

A method of fabricating a one crystalline phase lithium silicate glass ceramic and the manufacture of machinable blocks for dental appliances using a CAD/CAM device. The resulting glass ceramic contains a thermodynamically stable lithium silicate crystal through each of the steps of the process due to its specific material formulation.

7 Claims, 5 Drawing Sheets

LITHIUM SILICATE GLASS CERAMIC FOR FABRICATION OF DENTAL APPLIANCES

CROSS-REFERENCE TO CORRESPONDING APPLICATIONS

This application is a continuation-in-part of U.S. patent application Ser. No. 13/374,040 filed Dec. 8, 2011, currently pending, which, in turn, is a continuation-in-part of application Ser. No. 12/592,825 filed Dec. 3, 2009, now abandoned, which, in turn, is a continuation-in-part of application Ser. No. 12/283,472 filed Sep. 12, 2008, now issued as U.S. Pat. No. 7,892,995, which, in turn, is a continuation-in-part of application Ser. No. 12/082,576 filed Apr. 11, 2008, now abandoned.

BACKGROUND OF THE INVENTION

1. Field of the Invention

The present invention relates to a lithium silicate glass ceramic material and a process for fabricating that material for the manufacture of machinable blocks and subsequent fabrication of single crowns with the aid of a CAD/CAM device. The invention relates to a new version of such glass ceramic containing only lithium silicate as a main crystalline phase.

2. Background Art

There are many products available that employ lithium disilicate glass ceramic covered by several U.S. patents. Some of these patents claim a process for the preparation of shaped translucent lithium disilicate glass ceramic products from a mixture of basic components ($SiO_2$, $Al_2O_3$, $K_2O$, $Li_2O$, plus pigments and fluorescent oxides). The thermodynamic solid-liquid equilibrium of the system consisting of lithium oxide ($Li_2O$) and silicon dioxide ($SiO_2$) has been extensively studied even before that material was used as a dental ceramic (1-3, 5-6).

For those skilled in the art this experimental solid-liquid equilibrium can help explain how different glass ceramics can be obtained using the same two components when they are combined in different proportions. The same solid-liquid equilibrium shows what type of stable crystal is produced as a final product of crystallization when a specific mix composition of the two components is blended, melted, and crystallized to achieve the final product.

The crystallographic data for intermediate crystal compounds in the $Li_2O$—$SiO_2$ system is given by the Landolt-Borntein tables (4). The following are the types of crystal compositions possible in the $Li_2O$—$SiO_2$ system: $Li_8SiO_6$, $Li_4SiO_4$ or lithium orthosilicate monoclinic and orthorhombic; $Li_6Si_2O_7$, $Li_2SiO_3$ or lithium silicate; $Li_2Si_2O$ or lithium disilicate monoclinic and orthorhombic; and $Li_2Si_3O_7$ lithium trisilicate. Every crystal phase is formed based upon the initial molar ratio between the two components which can be 4, 3, 2 or 1 and any combination in between.

Thus when the silicon dioxide to lithium oxide molar ratio ($SiO_2/Li_2O$) is greater than or equal to two, meaning two moles of $SiO_2$ are mixed with one mole of $Li_2O$, the crystallized glass ceramic product will be mainly lithium disilicate ($2SiO_2.Li_2O$). This molar ratio of two is equivalent to a molar composition of lithium oxide in the binary mixture of 33% or 67% as $SiO_2$. When the same molar ratio is below 2.0, (i.e. 1.7) only lithium silicate crystals are produced ($Li_2O.SiO_2$). The lithium oxide molar composition for a ratio of 1.7 is equivalent to 37% molar or 63% as $SiO_2$. The type of resulting crystal due to the specific composition ratios gives to the glass ceramic its own distinguishable chemical and physical properties. Surprisingly, the same behavior is obtained if these two main components (silicon dioxide and lithium oxide) maintain their molar ratio below two even if they are mixed with other oxides as additives and modifiers. Such other common oxides are aluminum oxide, potassium oxide, calcium oxide, zirconium oxide and coloring oxides that are incorporated into the glass matrix and give the glass ceramic its final color and translucency.

Due to the final composition of this invention using a molar ratio of $SiO_2/Li_2O$ between 1.7 to 1.9, the only phase present is lithium silicate, instead of lithium disilicate, as a main constituent of the glass ceramic as a final product. This lithium silicate ($Li_2O.SiO_2$) in this composition is thermodynamically stable meaning that it does not suffer any change in its stoichiometric compositor through the entire process. Once it is formed the only change suffered is the increase in size of the crystals at the end of the process. That means that there is no formation of any metastable lithium metasilicate which is converted to a lithium disilicate ($2SiO_2.Li_2O$) when the molar ratio ($SiO_2/Li_2O$) of the formulation is higher or equal to 2. For example, a glass ceramic with a molar ratio of silicon dioxide to lithium oxide greater than or equal to two plus additional oxides will produce, after full crystallization a lithium disilicate glass ceramic with a melting temperature of 920° C. and a linear thermal coefficient of expansion of $10.5 \times 10^{-6}$/° C. as a final product and composition. In addition, during the production of this type of glass ceramic, the cast material is subjected to at least three different heat treatments: an annealing cycle for eliminating accumulated stresses, a nucleation cycle for the formation of lithium metasilicate or unstable lithium silicate, and finally a third thermal cycle to convert the unstable lithium silicate or metasilicate into a stable lithium disilicate. This complex mechanism is clearly shown in the following US patents:

Examples of those types of glass ceramics are claimed in Barret et al in U.S. Pat. No. 4,189,325 which discloses a lithium silicate glass ceramic where the raw materials are blended, melted at 1315° C. and held for 24 hours for homogenization, fritted and crushed, melted again and cast into preheated molds. They disclose a composition of silicon dioxide to lithium oxide molar ratio of two, producing a dental ceramic composed of lithium disilicate.

U.S. Pat. No. 4,480,044 to McAlinn discloses a glass ceramic formulation where the lithium silicate glass ceramic in their intermediate process stage has a thermal expansion of $13 \times 10^{-6}$/° C. and the lithium disilicate has a thermal expansion of $11.4 \times 10^{-6}$/° C. They disclose a machinable lithium disilicate glass ceramic with a percentage of silicon dioxide of 79.8%.

U.S. Pat. No. 4,515,634 to Wu et at discloses a castable glass ceramic composition useful as a dental restorative material. The components are blended and melted at 1400 to 1450° C., then quenched in water, dried, milled to a powder, and melted again at 1400° C. for 4 hours. Then the melt is cast into copper molds and transferred to the annealing process. The castable glass ceramic is lithium disilicate with a silicon dioxide to lithium oxide molar ratio of two, equivalent to silicon dioxide weight composition of 65%-74.7% and lithium oxide weight composition of 14.8-16.4%.

U.S. Pat. No. 5,219,799 to Beall et at discloses a lithium disilicate glass ceramic with silicon dioxide weight composition of 65%-80% and lithium oxide compositions of 8.0-19.0%. The blended raw materials are melted at 1450° C. for 16 hours and then poured into steel molds and annealed at 450° C.

U.S. Pat. No. 5,744,208 to Beall et at describes a lithium disilicate glass ceramic with silicon dioxide weight composition of 75%-95% and lithium oxide weight composition of 3-15%. The raw materials are blended, and then melted in the range of 1450-1600° C. for about 6-10 hours. The glass is then poured into steel molds. The glass is then annealed, nucleated and crystallized to produce lithium disilicate glass ceramic in the range of 500° C. to 850° C.

U.S. Pat. No. 5,968,856 to Scheweiger et al discloses a lithium disilicate glass ceramic with compositions of silicon dioxide weight between 57%-80% and lithium oxide composition 11-19%. The components are blended and melted at 1500° C. for one hour and then quenched, dried, milled, dry pressed and sintered to form blanks. The composition requires the addition of lanthanum oxide to improve the flow properties, control the crystal growth and eliminate the strong reaction of the material with the investment material used.

U.S. Pat. No. 6,514,893 to Scheweiger et al discloses a lithium disilicate glass ceramic with silicon dioxide composition of 57%-75% weight and lithium oxide composition 13-19% weight and also containing lanthanum oxide. The components are blended and fused into granulates and comminuted to a powder. Coloring oxides are then added, and the ceramic is pressed and heat treated.

U.S. Pat. No. 6,455,451 to Brodkin et al discloses a lithium disilicate glass ceramic with silicon dioxide composition of 62%-85% weight and lithium oxide composition 8-19% weight. They disclose a method of making the lithium disilicate by melting the components at 1200 to 1600° C., followed by quenching, drying, and heat treating to form the glass ceramic, followed by comminuting to a powder, compacting and sintering to a blank and pressing to form the restoration.

U.S. Pat. No. 6,517,623 to Brodkin et al discloses a pressable lithium disilicate glass ceramic where the components are melted in the range of 1200 to 1600° C., quenched, heat treated, comminuting the glass ceramic to a powder, and then compacting the powder to a starting blank before sintering the blank or the restoration.

U.S. Pat. No. 6,606,884 to Scheweiger et al describes a lithium disilicate glass ceramic where the components are mixed and melted at 1200 to 1650° C., followed by pouring the glass into water, milling and compacting, and placing the blank in a heat treatment to sinter.

U.S. Pat. No. 6,802,894 to Brodkin et al discloses a lithium disilicate glass ceramic with a silicon dioxide weight composition of 62%-85% and lithium oxide weight composition 8-19%. The components are mixed, melted at 1200 to 1600° C., and cast. The resulting glass is annealed at a range of 300 to 600° C., followed by subjecting the glass to a heat treatment from 400 to 1100° C.

U.S. Pat. No. 6,818,753 to Petticrew discloses a lithium disilicate glass ceramic with a silicon dioxide composition of 60%-80% weight and lithium oxide composition of 8-17% weight. The components are blended, melted, quenched, heat treated, milled to a powder, dry pressed, and hot pressed into the desired restoration.

Scheweiger et al U.S. Pat. No. 7,316,740 B2 claims a lithium silicate glass ceramic with silicon dioxide weight compositions of 64 to 73% and lithium oxide weight compositions of 13 to 17%. The lithium disilicate final product is demonstrated by means of a XRD pattern (FIG. 6) and DSC phase transformation curve from lithium metasilicate to lithium disilicate (FIG. 2). The DSC diagram shows the change in energy from the stage of metasilicate to disilicate, which is only necessary if lithium disilicate is desired to be the crystal phase used as a final product.

U.S. Pat. No. 7,452,836 to Apel et al discloses a lithium silicate glass ceramic with silicon dioxide composition of 64%-75% weight and lithium oxide composition of 13-17% weight producing lithium disilicate as a final product. They also describe a glass ceramic with a molar ratio of silicon dioxide to lithium oxide of at least 2.3.

U.S. Pat. No. 7,867,930 to Apel et al shows a lithium silicate glass ceramic with silicon dioxide composition of 64%-75% weight and lithium oxide composition of 13-17% weight producing lithium disilicate as a final product.

U.S. Pat. No. 7,871,948 to Apel et al describes a lithium silicate glass ceramic with silicon dioxide composition of 64%-75% weight and lithium oxide composition of 13-17% weight, producing lithium disilicate as a final product. The glass of the starting material is subjected to an initial heat treatment to form lithium metasilicate or unstable lithium silicate and then goes through a second heat treatment to convert the lithium metasilicate to a lithium disilicate.

U.S. Pat. No. 7,867,931 to Apel et al discloses a lithium silicate glass ceramic with silicon dioxide composition of 64%-75% weight and lithium oxide composition of 13-17% weight producing lithium disilicate as the final product. They also describe a glass ceramic with a molar ratio of silicon dioxide to lithium oxide in the range of 2.3 to 2.5.

U.S. Pat. No. 8,042,358 to Schweiger et al discloses a lithium silicate glass ceramic with silicon dioxide composition of 65%-70% weight and lithium oxide composition of 14-16% weight producing lithium disilicate as the final product. In their specific process the raw materials such as carbonates, oxides and phosphates are prepared and melted in the range of 1300-1600° C. for 2 to 10 hours. They explain that in order to obtain a particularly high degree of homogeneity, the glass melt obtained may be poured into water to form glass granulates and the glass granulates obtained are melted again.

U.S. Pat. No. 7,816,291 to Schwinger et al, discloses a lithium silicate dental glass ceramic where the starting glass uses a very specific composition and a specific process to provide in the intermediate stage a glass ceramic which consists of metastable lithium metasilicate. Then after machining the metastable lithium metasilicate, it is converted by two heat treatments into a lithium disilicate glass ceramic product with outstanding mechanical properties, excellent optical properties and very good chemical stability thereby undergoing only a very limited shrinkage. The metastable phase definition is broadly accepted by those skilled in the art as a thermodynamic unstable crystalline phase of lithium metasilicate which, when heated, disappears to allow the formation of a thermodynamic stable crystal phase form such as lithium disilicate. This is only possible for the specific composition used in this and all the prior art mentioned above.

For those skilled in the art it is well understood that the lithium oxide and silicon dioxide binary system has been extensively studied and several patents for dental glass ceramics have been granted in the last few years. However all the research so far falls in a range where lithium disilicate is formed as a final product and none of the references cited above discloses a lithium silicate glass ceramic as a final product. For those skilled in the art it is evident that the type of crystal produced depends exclusively on the molar ratio of silicon dioxide to lithium oxide in the glass ceramic and not the additives or modifiers added to the mixture. This molar ratio controls the type of crystal formed in the final composition and furthermore gives its name to the final glass ceramic.

More surprisingly, in the present invention and due to our specific formulation, there is no metastable lithium metasilicate in the intermediate stage or in the stage where the material can be easily machined into the shape of dental restorations. Instead a lithium silicate crystal which is thermodynamically stable is formed, keeping its stoichiometric composition through the entire process and therefore only grown as lithium silicate during the final stage of the process. As consequence no lithium disilicate is formed in the final stage of the process.

Most of the existing patents in the dental field describe the use the same basic components. The present invention uses germanium dioxide as a fundamental part of the formula. This oxide is broadly used in glass preparation for its good optical properties. The oxide has been well studied and has positive effects compared to common silicon glasses. It has been found that the addition of germanium oxide produces a melt with low viscosity, which facilitates the castability of the process and increases the thermal expansion and the refractive index of the resulting lithium silicate glass ceramic. More importantly, the addition of germanium dioxide increases the final density of the glass resulting in higher values of flexural strength than the lithium disilicate glasses free of germanium dioxide. U.S. Patent Application Publication No. 2004/0197738 to Ban et al discloses a process to make dental frame of zirconium-yttrium sintered ceramics and they describe dental porcelain with germanium oxide as a joint component different than the zirconium yttrium oxide frame. However germanium oxide is not used as a component of the framework ceramic network. It is used only in formulation of the ceramic joint and is just a part of a series of other oxides that can be joined to the framework material.

Due to the low silicon dioxide to lithium oxide molar ratio of 1.7 of the present invention, equivalent to 37% molar of lithium oxide (63% as silicon dioxide) the ceramic has a lower melting point compared to the glass ceramic of the prior art. In addition, this new glass ceramic contains the lowest silicon dioxide weight percent compared to all of the noted prior art. Therefore, due to this specific composition of lithium oxide in the mixture, the type of resulting crystal after crystallization (lithium silicate) gives to the glass ceramic its own chemical and physical properties, which makes it completely distinguishable from the prior glass ceramics noted above. Due to this distinguishable composition, the glass ceramic of the present invention, has a lower melting temperature which can be made even lower with the addition of germanium oxide. Germanium oxide replaces silicon dioxide in the glass network, causing it to have a negative effect on the resulting melting point compared to a glass ceramic containing only silicon dioxide. Thus the processing and optimal melting temperature is in the range of 1100° C. to 1200° C. instead of 1200° C. to 1650° C. of the U.S. patents cited above and specifically compared to U.S. Pat. No. 6,514,893 to Schweiger et al. The glass ceramics mentioned in the prior art patents cannot be cast in the range of 1100° C. to 1200° C. because they are too viscous due to their high silicon dioxide content therefore the processes disclosed in prior art patents with higher melting temperatures should be used. The present process will result in a more economical production because the energy employed for melting the glass is considerably lower and there are lower energy loses by radiation compared to the Schweiger process.

In addition to having a process with lower energy consumption, another significant improvement of the inventive process is related to the mixing and reaction of the components. In all of the cited prior art patents, the mix of the components is blended and melted at 1400 to 1650° C. and then cast or quenched in water. The quenched glass powder is dried, milled, and melted again in order to improve the homogeneity and the quality of the product. Surprisingly, we found that the first melting and casting process can be avoided if we perform a calcination process on the mixture of raw materials to a temperature in the range of 700 to 800° C. without melting the components. At this stage, all the raw materials in the form of salts (such as lithium carbonate as the source of lithium oxide, calcium carbonate as the source of calcium oxide, and di-ammonium phosphate as the source of phosphorous oxide) are decomposed, eliminating gases such carbon dioxide and ammonia, producing a ceramic powder free of gases. After cooling down, the calcined mix is milled again, producing a homogeneous powder with a very small particle size. The final step is melting and casting in the range of 1100° C. to 1200° C., resulting in a homogeneity of all the components. In addition, by eliminating the gases during the calcination process, the cast glass becomes bubble free, making this a significant advantage over the processes described in the prior art The present invention is also unique compared to those in the prior art due to its composition. The use of a low melting temperature is only possible with the inventive glass ceramic because of the low content of silicon dioxide and the high content of lithium oxide. This translates to a molar oxide ratio ($SiO_2/Li_2O$) below 2.0, (i.e., 1.7) in which only lithium silicate crystals are produced ($SiO_2$—$Li_2O$). In addition to the composition, we have implemented a process for our glass ceramic that produces a homogeneous product and that can be used only with our specific formulation. This process cannot be used with the other prior art glass ceramics due to the lower operating temperatures.

It is emphasized that in the present glass ceramic the silicon dioxide and lithium oxide molar ratio content ($SiO_2/Li_2O$) is less than 2, specifically the oxide molar ratio is preferably about 1.7. This is specifically equivalent to 63% molar of silicon dioxide and 37% molar of lithium oxide, and specifically equivalent in the overall formulation of about 56% weight percent of all of the glass ceramic as silicon dioxide and 16.0% weight percent as lithium oxide and the remaining 28% composed of the oxide additives and modifiers. In all of the glass ceramic, only lithium silicate ($Li_2O.SiO_2$) crystals are produced as the final crystal phase product. During the heating process of the glass, the first crystals formed are stable lithium silicate and not metastable lithium metasilicate and such crystals remain stable through the end of the growing process. This means that there is no need for a third thermal process for producing the final crystal of lithium silicate making this an additional beneficial characteristic unique to the present invention. This new ceramic has a softening temperature of about 700 to 800° C. and a linear thermal coefficient of expansion of about 12 to $12.5 \times 10^{-6}$/° C. as a final product and a composition yielding completely different chemical and physical properties compared to the prior art. This is easily demonstrated in commonly assigned U.S. patent application Ser. No. 12/1592,825, paragraph [0012], FIG. 1 showing a XRD pattern diffraction where only lithium silicate crystals are present in the final product and in paragraph [0013] thereof where the glass ceramic is shown to have a percentage linear change of 0.55% measured at 500° C. and an equivalent coefficient of thermal expansion of $11.5 \times 10^{-6}$/° C.

The following is a list of non-patent references noted herein:
1. BOROM, P. et al, Strength And Microstructure In Lithium Disilicate Glass-Ceramics. The authors prepare lithium disilicate glass ceramics and measured the differences between the thermal expansion of the lithium disilicate with a value of $13 \times 10^{-6}$/° C. and lithium silicate with a value of $11.4 \times 10^{-6}$/° C. After the heat treatment above 800° C. the only phase present is lithium disilicate for a glass ceramic composition of 71.8% of silicon dioxide and 12.6% of lithium oxide.
2. EPPLER, A., Glass Formation And Recrystallization In The Lithium Metasilicate Region Of The System $Li_2O—Al_2O_3—SiO_2$ J. Am. Ceram. Soc., 46, {2}, 97-101, (1963).
3. HUMMEL, F. A., Thermal Expansion Properties Of Some Lithia Minerals, J. Am. Ceram. Soc., 34{8} 235-39. (1951).
4. LANDOLT-BÖRNSTEIN (LB), Zahlenwerte und Funktionen aus Physik, Chemie, Astronomie, Geophysik und Technik.
5. S. CLAUS et al, Phase Equilibria In The $Li_4SiO_4$—$Li_2SiO_3$ Region Of The Pseudobinary $Li_2O—SiO_2$, Journal of Nuclear Materials, Volume 230, Issue 1, May 1996, Pages 8-11.
6. SHERMER, HERMAN, Thermal Expansion Of Binary Alkali Silicate Glasses, Journal of Research of the National Bureau of Standards. Vol. 57, No. 2, August 1956. The author prepares lithium silicate glasses with silicon oxide and lithium oxide molar ratio below 2.0 being lithium silicate with thermal expansion between 12 and $14.77 \times 10^{-6}/°$ C. There is no lithium disilicate using this chemical molar composition.

SUMMARY OF THE INVENTION

The present invention relates to preparation of an improved lithium silicate glass ceramic for the manufacture of blocks for dental appliance fabrication using a CAD/CAM process and hot pressing. The lithium silicate material has a chemical composition that is different from those reported in the prior art, especially because of the use of germanium dioxide in the formulas and a low silicon dioxide content. The softening points are close to the crystallization final temperature of 800° C. indicating that the samples will support the temperature process without shape deformation.

The initial components are chemical precursors, specifically aluminum hydroxide for aluminum oxide, boric acid for boron oxide, lithium carbonate for lithium oxide, ammonium hydrogen phosphate or calcium phosphate for phosphorus pentoxide, zirconium silicate or yttrium stabilized zirconia for zirconium oxide, calcium carbonate for calcium oxide, lithium fluoride for lithium oxide and fluoride, and potassium carbonate for potassium oxide. The remaining elements are single oxide precursors of silicon, cerium, titanium, tin, erbium, vanadium, germanium, samarium, niobium, yttrium, europium, tantalum, magnesium, praseodymium, and vanadium oxides.

The components are carefully weighed and then mechanically blended using a V-cone blender for about 5 to 10 minutes. Then in order to achieve uniform particle size of the components, the mixture undergoes a ball mill process for two hours. The powder obtained is put into large alumina crucibles and undergoes calcination to 800° C. for about 4 hours. In this stage the carbonate precursors, lithium carbonate, calcium carbonate, potassium carbonate, decompose releasing carbonic gas and producing the corresponding pure oxides, lithium oxide, calcium oxide and potassium oxide, respectively. In the same process the other chemical precursors, ammonium phosphate, aluminum hydroxide and boric acid also release nitrogen gases and water, producing the corresponding pure oxides, phosphorous pentoxide, aluminum oxide and boron oxide, respectively. At this stage of calcination the original powder mix loses approximately 25% of its original weight due to the evaporation losses. Also, the first reactions between the pure oxides take place in this stage, but there is never any melting of the components and no reaction takes place with the alumina crucible. After cooling down, the blend of components undergoes ball milling again, producing a homogeneous, gas free, fine powder with a particle size below 30 microns. The calcined powder can be safely stored in plastic containers for extended periods of time without any gas release and can be used any time for the next step of the process.

In the final stage of the process, the calcined powder is melted in a platinum crucible at a temperature of 1200° C. with a holding time of about 2 hours before casting. The melt with the appropriate viscosity is cast continuously over graphite molds. Surprisingly, the glass cast is bubble free due to the prior elimination of the gases during the calcination step. This constitutes a significant advantage over the processes described in the prior art. Due to the calcination process step, there is no need for a second re-melting process for improving homogeneity. The glass cast is then subjected to an annealing step followed by an intermediate crystallization step or a full crystallization step depending on what is desired as a final product.

Due to the specific molar ratio of silicon dioxide and lithium oxide (1.7/1) used in the preferred embodiments of the present invention, the only preferred crystal structure formed is lithium silicate ($SiO_2.Li_2O$) in the intermediate or full crystallized product. Surprisingly we found that in this invention, the crystal growth process can be momentarily stopped at any temperature interval between the ranges of 350° to 800° C. and then the crystal can continue growing by heating it again to reach the optimal size at 800° C. Above 800° C. the sample starts melting and the reverse process of dissolving the crystals in the glass matrix takes place.

Thus in the present invention, the intermediate crystallization process step is easily controlled by stopping the heating process at 600° C. and cooling down to room temperature. It can then be heated again to 800° C. for achieving the full crystallized product. Thus if we take the intermediate block material of lithium silicate, after the thermal heat process from room temperature to 600° C., it can be milled to a dental restoration using conventional CAD/CAM devices and then it can be heated up again to 800° C. continuing towards maximum crystal growth and achieving the optimal physical properties. Surprisingly, the same formulation, after a thermal process from room temperature to 800° C., can be easily hot pressed in the range of 800-840° C. using conventional all ceramic dental investments and commercial press furnaces (i.e., Whip Mix Pro-Press 100). For the hot press process, the dental restoration is milled in a wax block, followed by investing the wax pattern using commercial all ceramic investments. After firing the investment, the wax is burned out, allowing the cavity of the restoration to become available to fill with the ceramic. After hot pressing, the restoration achieves the optimal physical properties.

The same formulation produces the same lithium silicate crystalline phase through all the thermal process steps and the dental restoration can be optimally achieved by using either CAD/CAM or hot press techniques. Being able to achieve this with the same formulation is a unique and advantageous characteristic compared to the prior art.

BRIEF DESCRIPTION OF THE DRAWINGS

The aforementioned objects and advantages of the present invention, as well as additional objects and advantages thereof, will be more fully understood herein after as a result of a detailed description of a preferred embodiment when taken in conjunction with the following drawings in which.

DETAILED DESCRIPTION OF PREFERRED EMBODIMENTS

The prior art materials are based on the formation of lithium disilicate materials. A principal object of the present invention is to prepare a controlled lithium silicate glass ceramic using in the formulation a specific silicon dioxide and lithium oxide molar ratio with excellent physical properties for manufacturing dental restorations. The glass material subjected to a heat treatment produces an optimal lithium silicate crystal forming a glass ceramic product with outstanding mechanical properties, excellent optical properties, a very good chemical solubility, little contraction and high flexural strength values.

The lithium silicate of the present invention preferably comprises the following components and compositions:

| Component | weight % composition | |
|---|---|---|
| | minimum | maximum |
| $SiO_2$ | 53.0 | 57.0 |
| $Al_2O_3$ | 3.0 | 5.0 |
| $K_2O$ | 3.0 | 5.0 |
| CaO | 0.0 | 1.0 |
| $B_2O_3$ | 0.0 | 2.0 |
| $CeO_2$ | 0.0 | 1.0 |
| MgO | 0.0 | 1.0 |
| Fluorine | 0.0 | 1.0 |
| $Li_2O$ | 14.0 | 17.0 |
| $ZrO_2$ | 4.0 | 6.0 |
| $TiO_2$ | 0.0 | 3.0 |
| $P_2O_5$ | 2.0 | 3.0 |
| SnO | 0.0 | 1.0 |
| $Er_2O_3$ | 0.0 | 2.0 |
| $V_2O_5$ | 0.0 | 1.0 |
| $GeO_2$ | 0.5 | 8.0 |
| $Ta_2O_5$ | 0.0 | 3.0 |
| $Sm_2O_3$ | 1.0 | 6.0 |
| $Pr_2O_3$ | 0.0 | 1.0 |
| $Eu_2O_3$ | 0.0 | 2.0 |
| $Y_2O_3$ | 0.0 | 5.0 |
| $Nb_2O_5$ | 0.0 | 1.0 |

The invention is explained in more detail below with the following examples:

The sample preparation and its elemental oxide composition are listed in Table 1.

TABLE 1

| | Components % weight | | | | |
|---|---|---|---|---|---|
| | Example 1 | Example 2 | Example 3 | Example 4 | Example 5 |
| $SiO_2$ | 55.03 | 56.19 | 56.21 | 56.21 | 53.88 |
| $Al_2O_3$ | 4.09 | 4.18 | 4.18 | 4.18 | 3.11 |
| $K_2O$ | 4.42 | 4.52 | 4.52 | 4.52 | 3.44 |
| CaO | 0.94 | 0.96 | 0.96 | 0.96 | 0.00 |
| $B_2O_3$ | 1.58 | 1.61 | 1.61 | 1.61 | 0.00 |
| $CeO_2$ | 0.21 | 0.65 | 0.34 | 0.41 | 0.63 |
| MgO | 0.22 | 0.23 | 0.23 | 0.23 | 0.00 |
| Fluorine | 0.49 | 0.50 | 0.50 | 0.50 | 0.00 |
| $Li_2O$ | 15.81 | 16.14 | 16.15 | 16.15 | 14.81 |
| $ZrO_2$ | 4.70 | 4.79 | 4.80 | 4.80 | 4.88 |
| $TiO_2$ | 2.40 | 0.80 | 0.80 | 0.80 | 0.63 |
| $P_2O_5$ | 2.52 | 2.58 | 2.58 | 2.58 | 2.94 |
| SnO | 0.22 | 0.07 | 0.13 | 0.12 | 0.00 |
| $Er_2O_3$ | 0.37 | 0.76 | 0.36 | 0.21 | 1.26 |
| $V_2O_5$ | 0.39 | 0.22 | 0.26 | 0.11 | 0.03 |
| $GeO_2$ | 0.90 | 0.92 | 0.92 | 0.92 | 7.75 |
| $Ta_2O_5$ | 0.07 | 0.15 | 0.22 | 0.01 | 0.00 |
| $Sm_2O_3$ | 2.03 | 4.09 | 4.07 | 4.09 | 5.71 |
| $Pr_2O_3$ | 0.03 | 0.33 | 0.04 | 0.00 | 0.88 |
| $Eu_2O_3$ | 0.00 | 0.00 | 0.00 | 1.25 | 0.05 |
| $Y_2O_3$ | 3.13 | 0.11 | 0.61 | 0.36 | 0.00 |
| $Nb_2O_5$ | 0.46 | 0.22 | 0.53 | 0.00 | 0.00 |
| TOTAL | 100.00 | 100.00 | 100.00 | 100.00 | 100.00 |
| | Example 6 | Example 7 | Example 8 | Example 9 | Example 10 |
| $SiO_2$ | 54.08 | 54.49 | 56.17 | 53.49 | 56.19 |
| $Al_2O_3$ | 3.12 | 3.86 | 4.18 | 3.98 | 4.18 |
| $K_2O$ | 3.45 | 4.20 | 4.52 | 4.30 | 4.52 |
| CaO | 0.00 | 0.00 | 0.96 | 0.92 | 0.96 |
| $B_2O_3$ | 0.00 | 0.00 | 1.61 | 1.53 | 1.61 |
| $CeO_2$ | 0.95 | 0.64 | 0.00 | 0.20 | 0.62 |
| MgO | 0.00 | 0.00 | 0.23 | 0.22 | 0.23 |
| Fluorine | 0.00 | 0.00 | 0.50 | 0.48 | 0.50 |
| $Li_2O$ | 14.85 | 15.25 | 16.15 | 15.37 | 16.14 |
| $ZrO_2$ | 4.89 | 4.88 | 4.80 | 4.56 | 4.79 |
| $TiO_2$ | 0.63 | 0.64 | 0.80 | 0.78 | 0.80 |
| $P_2O_5$ | 2.95 | 2.97 | 2.58 | 2.45 | 2.58 |

TABLE 1-continued

| Components % weight | | | | | |
|---|---|---|---|---|---|
| SnO | 0.00 | 0.00 | 0.00 | 0.00 | 0.07 |
| $Er_2O_3$ | 1.52 | 1.28 | 0.05 | 0.16 | 0.61 |
| $V_2O_5$ | 0.06 | 0.04 | 0.00 | 0.48 | 0.15 |
| $GeO_2$ | 7.77 | 7.70 | 0.92 | 0.87 | 0.92 |
| $Ta_2O_5$ | 0.00 | 0.00 | 2.33 | 0.00 | 0.18 |
| $Sm_2O_3$ | 4.82 | 3.34 | 1.83 | 4.90 | 4.05 |
| $Pr_2O_3$ | 0.90 | 0.72 | 0.00 | 0.23 | 0.24 |
| $Eu_2O_3$ | 0.00 | 0.00 | 0.05 | 0.00 | 0.00 |
| $Y_2O_3$ | 0.00 | 0.00 | 2.33 | 4.90 | 0.24 |
| $Nb_2O_5$ | 0.00 | 0.00 | 0.00 | 0.18 | 0.45 |
| TOTAL | 100.00 | 100.00 | 100.00 | 100.00 | 100.00 |

A particularly preferred lithium silicate material as described in the examples 1 to 10 comprises 53 to 59 wt. % of $SO_2$, 14 to 19% wt. of $Li_2O$ and 1 to 9% of $GeO_2$, where after nucleation only lithium silicate is formed and then after complete crystal growth only lithium silicate crystals are formed.

The lithium silicate material of this invention is preferably produced by a process which comprises the following steps:
(a) A mix of the precursors of the final components of the table 1, are blended together for 10 to 30 min until a mechanical mix is obtained.
(b) The mix is ball milled dry or wet using zirconia media for about 1 to 2 hours to homogenize the components and achieve almost the same particle size in all the components.
(c) The sample is calcined at 800° C. for about to 4 hours in order to decompose the precursors to their primary oxides and eliminate any possibility of formation of gas after the process.
(d) Ball-mill the sample of step (c) in order to produce a powder with an average particle size below 30 microns.
(e) The powder of step (d) is melted in a platinum crucible at a temperature between 1100 to 1200° C. for 1 to 2 hours. It is then poured into cylindrical or rectangular graphite molds and cooled down to room temperature.
(f) The glass ceramic of step (e) is then subjected to an intermediate crystal growth process at a temperature of from room temperature to 600° C. for 10 to 60 min. The growth of the lithium silicate crystals is temporarily stopped for the desired intermediate size by cooling the glass ceramic to room temperature.
(g) The glass ceramic of step (f) is subjected to a single step heating cycle from room temperature to 800° C. to achieve full crystallization.
(h) For use in a CAD-CAM milling device, the dental restoration is made using a block after intermediate process step (f). After milling, the restoration is heated again from 350° C. to 800° C. or to full crystallization step (g) where the optimal lithium silicate crystal growth in the glass ceramic is achieved in a single step program.
(i) For an alternative hot pressing technique, the sample after [step (g)] is pressed into a dental restoration at a temperature of 800-840° C., where the optimal lithium silicate crystal growth in the glass ceramic is achieved.

Coefficient of Thermal Expansion and Softening Point

The percentage linear change vs. temperature was measured using an Orton dilatometer. The coefficient of thermal expansion at 500° C. and the softening point were calculated for all the samples. For this purpose a rectangular rod of approximately 2 inches long was cast and then subjected to the intermediate crystallization cycle at 600° C. for 40 min. After this process the rod is cut into two parts. One part is used for measuring transition temperature, softening point temperature, and coefficient of thermal expansion of that process step. The second part is fully crystallized at 800° C. for about 10 minutes and is used for measuring the same properties. It is expected that after the crystallization step, the softening temperature point increases for the samples due to the formation of larger lithium silicate crystals. Test results are displayed in Table 2.

Flexural Strength

Biaxial flexural strength tests (MPa) were performed following ISO-6872 procedures. Ten round samples were cut, ground gradually and polished to a mirror finish in the intermediate stage of step (f). The samples were then fully crystallized in a single stage program from 350° C. to 800° C. for 10 minutes. Then the biaxial flexural strength was measured. For the hot pressing technique the glass ceramic of sample of step (g) is hot pressed into round discs in the interval of 800 to 840° C. Then the discs are ground gradually and polished to a mirror finish, heated as a simulated glaze cycle, and tested. Test results expressed in MPa are displayed in Table 2.

Chemical Solubility

A chemical solubility test was performed according to ISO-6872. Ten discs samples subjected to step (g) are placed in a glass flask with an aqueous solution of 4% (V/V) of acetic acid analytical grade (Alfa Aesar). The flask is heated to a temperature of 80+/−3° C. for 16 hours. The change in weight before and after the test is determined and then the chemical solubility expressed as $\mu g/cm^2$ is calculated and shown in Table 2.

TABLE 2

Physical Properties of the Lithium silicate glass ceramic

| | Example #2 | Example #3 | Example #4 | Example #5 | Example #8 |
|---|---|---|---|---|---|
| Softening temperature, ° C., Intermediate stage at 600° C. | 689 | 618 | 690 | 766 | 711 |
| Softening temperature, ° C. crystallized sample at 800° C. | 727 | 744 | 717 | 789 | 724 |
| Coefficient of expansion, $X10^{-6}/°$ C. Crystallized sample at 800° C. | 11.81 | 12.58 | 12.27 | 11.30 | 11.61 |
| Flexural strength, MPa, Crystallized at 800° C. | 350+/−28 | 402+/−56 | 359+/−40 | 365+/−60 | 370+/−50 |
| Flexural strength, MPA Hot pressed sample | 393+/−48 | 423+/−61 | 533+/−39 | 345+/−20 | 397+/−57 |
| Chemical Solubility, $\mu g/cm^2$ Crystallized sample at 800° C. | 72 | 58 | 65 | 39 | 58 |

TABLE 3

Quantitative analysis of the crystalline phases of Lithium Silicate intermediate stage and fully crystallized stage with average crystal size

| | Quantitative Phase Analysis (wt. %) | |
|---|---|---|
| Chemical formula | Lithium Silicate partially crystallized at 600° C. | Lithium Silicate fully crystallized at 800° C. |
| $Li_2SiO_3$ | 43.1% (183Å) | 54.1% (767Å) |
| $Li_3PO_4$ | | 5.3% (738Å) |
| Amorphous | 56.9% | 40.6% |

Figure 1:
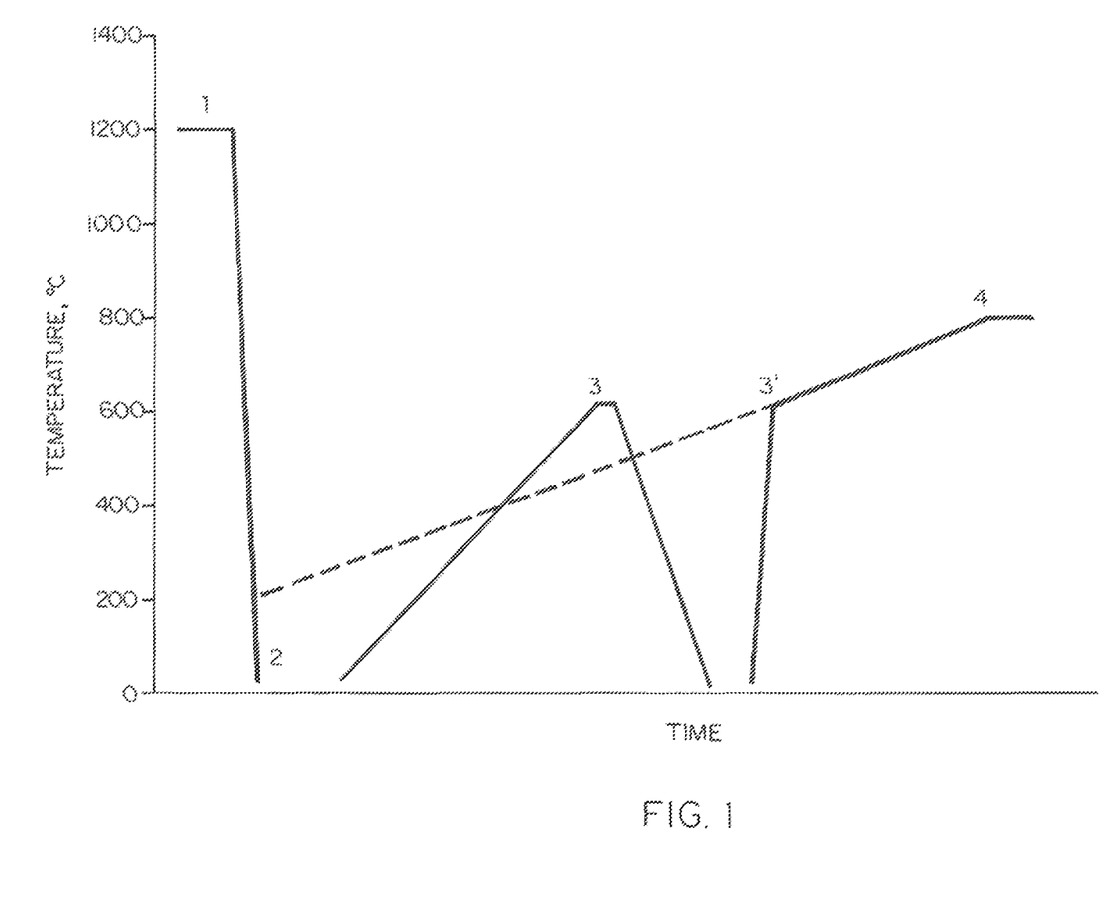
FIG. 1 shows the thermal pattern profile employed for this invention from the melting glass temperature to the formation in a one or two step process of the stable lithium silicate glass ceramic. For the one step process, the cast glass ceramic is heated from point 2 to point 4. For the two step process, the cast glass ceramic is heated from point 2 to point 3 and then after milling the dental restoration is heated again from point 3 to point 4. In the first stage of the process (2 to 3), the size of the crystals of lithium silicate are controlled to a specific size and its growing process stopped by decreasing the temperature. Then in the second step the same crystals formed in step 1 continue to growth during heating again in order to achieve the appropriate crystal size.
Figure 2:
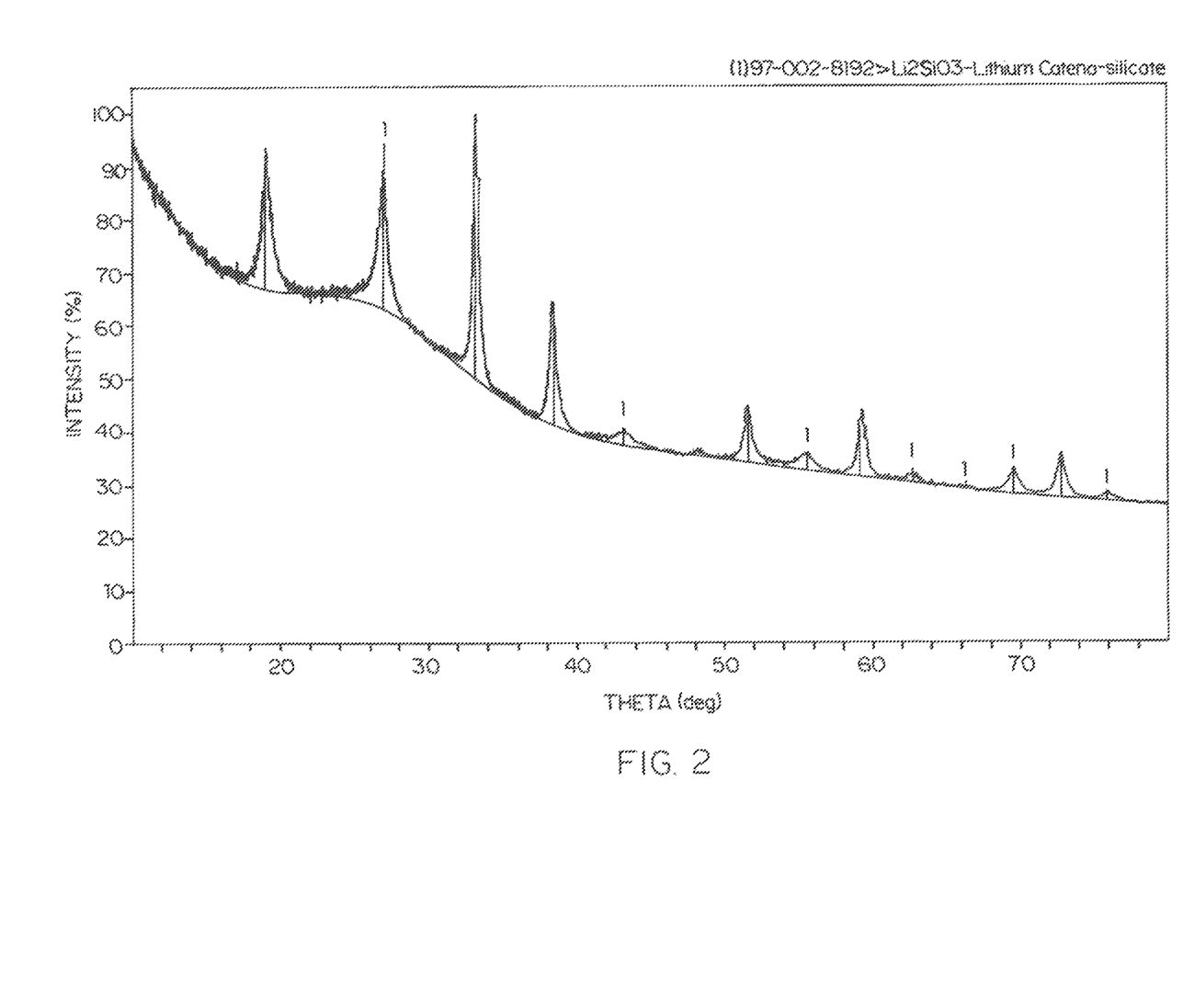
FIG. 2 is an XRD diffraction pattern of a sample of the invention after the intermediate crystallization step (from room temperature to 600° C.) showing the presence of lithium silicate as a main constituent phase in the glass ceramic composition.
Figure 3:
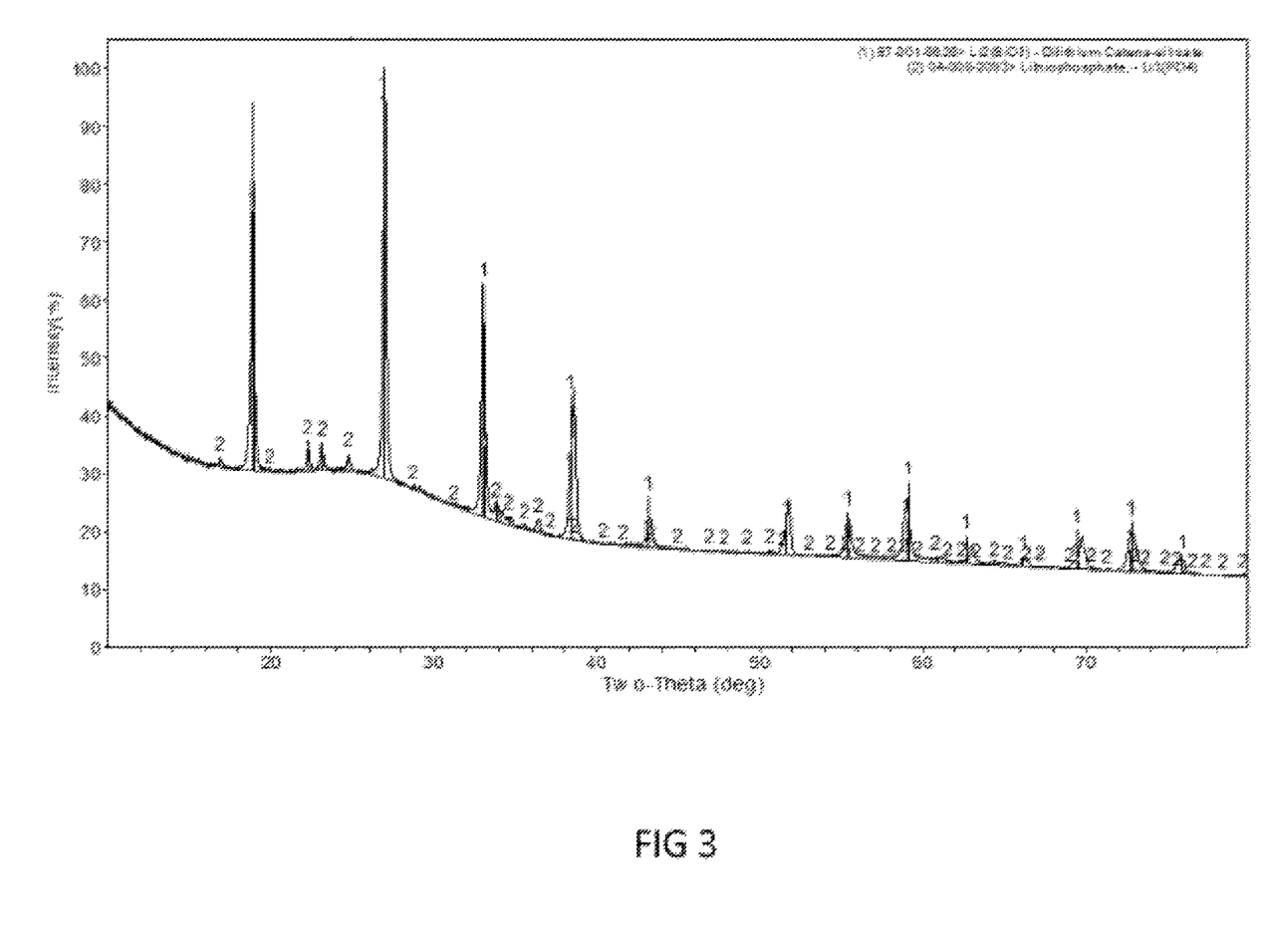
FIG. 3 is an XRD diffraction pattern of a sample of the invention after the full crystallization step (from room temperature to 800° C.) showing the presence of lithium silicate as a main constituent phase in the glass ceramic composition. Because the molar ratio of $SiO_2/Li_2O$ is between 1.7 to 1.9, the crystallized phase of the final material shows the presence of mainly lithium silicate and no lithium disilicate.
Figure 4:
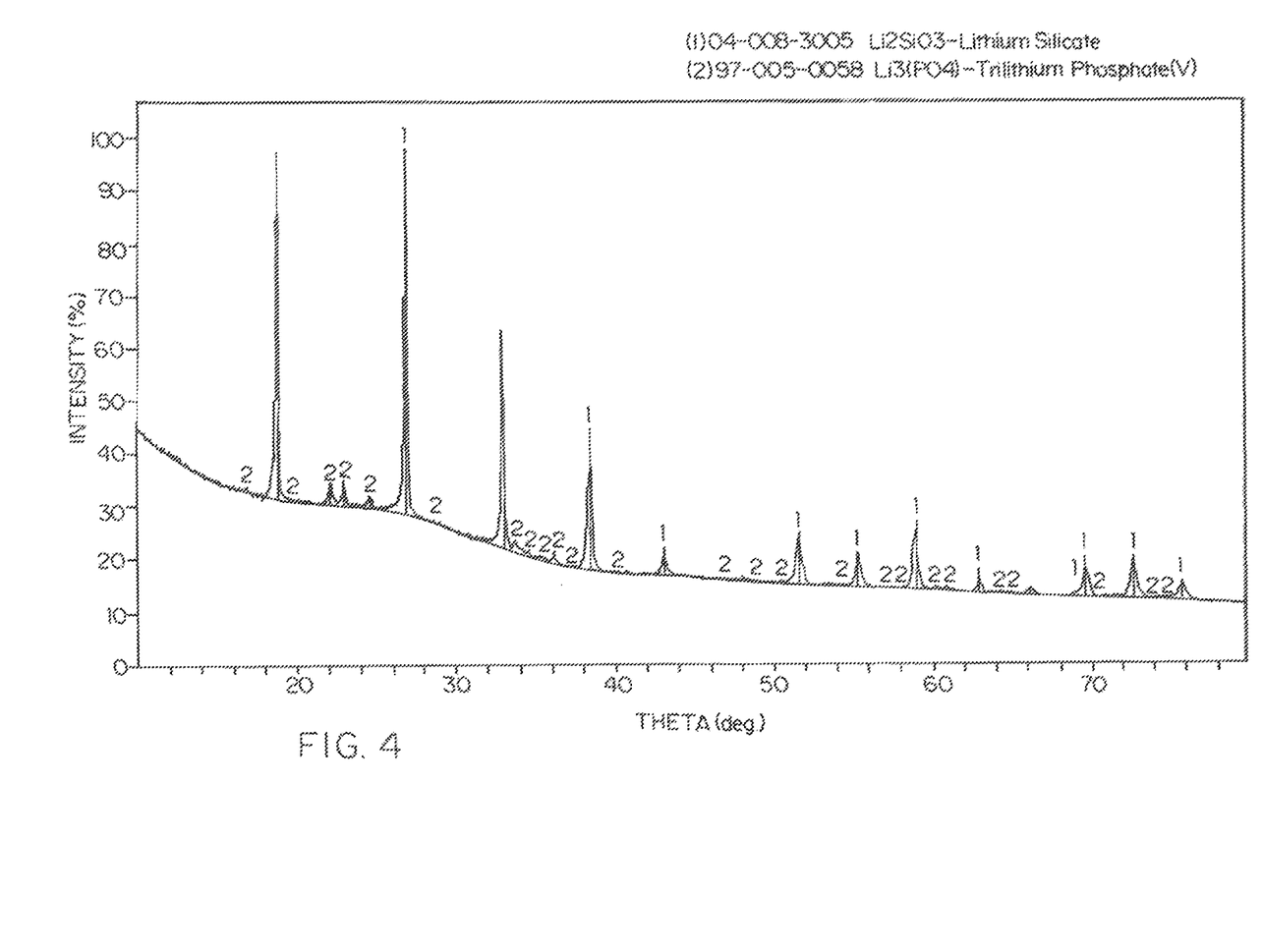
FIG. 4 is an XRD diffraction pattern of a sample of this invention after hot pressing in the interval of 800° C. to 840° C. showing the presence of lithium silicate as a main constituent phase in the glass ceramic composition. Because the molar ratio of $SiO_2/Li_2O$ is between 1.7 to 1.9, the crystallized phase of the final material shows the presence of mainly lithium silicate and no lithium disilicate.
Figure 5:
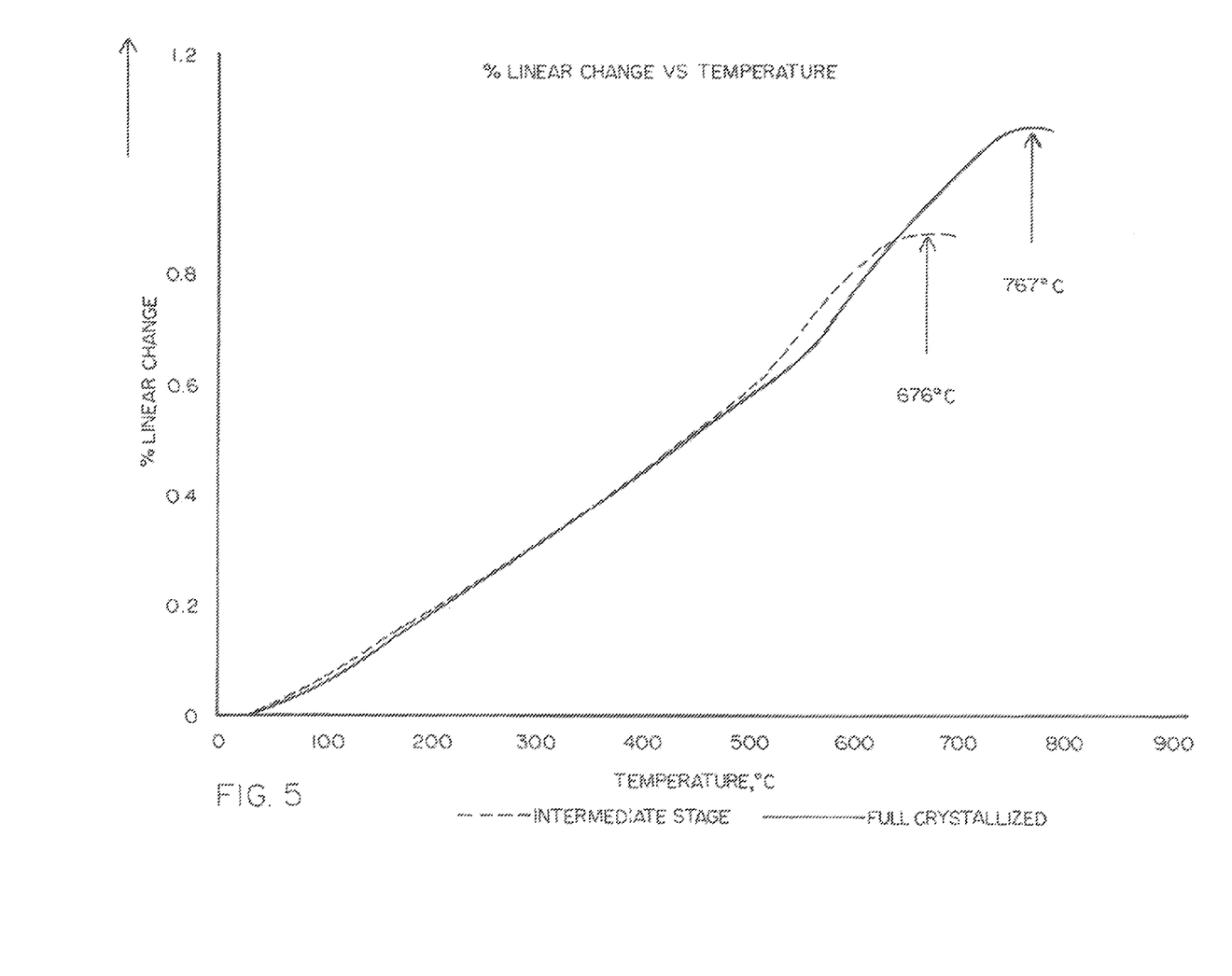
FIG. 5 is a graphical illustration of a dilatometric measurement of a sample of the invention resulting from full crystallization. The softening temperature of the intermediate step is lower than the temperature after full crystallization This is due to the crystal growth after heating the glass in the intermediate stage from room temperature to 800° C.

The table 3 shows the quantitative analysis of the crystalline phases present in the two samples. The partially crystallized sample contains mainly Lithium silicate whereas the fully crystallized sample contains 91% as lithium silicate and 9% as lithium phosphate of the total crystalline phases present. Only two heating steps are necessary (FIG. 1). For the one step process the casted glass ceramic is heated from 2 to 4 of the graph of FIG. 1. For the two step process the casted glass ceramic is heated from 2 to 3 of the graph of FIG. 1 and then after milling the dental restoration heated again from 3 to 4. In the first stage of the process (2 to 3), the size of the crystals of lithium silicate are controlled to an average value of 183 Angstroms. At this crystal size stage the glass material can be easily milled to a dental restoration using conventional CAD/CAM devices. Then the growing process is stopped by decreasing the temperature and subsequence increase in the glass viscosity. Then in the second step the same crystals formed in step 1 continue to growth during heating again to a size averaging 770 Angstroms. Those values are calculated from the XRD patterns. The lithium silicate glass ceramic produced by this process achieves an extraordinary translucency and shade that resemble natural teeth. The total weight percentage of the crystalline phase achieved is about 60%. During these two heating steps, the mainly crystal phase present is lithium silicate and there is no lithium disilcate.

The preferred range composition (in % of this glass ceramic material is the following:

TABLE 4

Preferred Range of Composition Components

| | weight % composition | |
|---|---|---|
| Component | minimum | maximum |
| $SiO_2$ | 53.5 | 56.2 |
| $Al_2O_3$ | 3.1 | 4.2 |
| $K_2O$ | 3.4 | 4.5 |
| CaO | 0.0 | 1.0 |
| $B_2O_3$ | 0.0 | 1.6 |
| $CeO_2$ | 0.0 | 1.0 |
| MgO | 0.0 | 0.2 |
| Fluorine | 0.0 | 0.5 |
| $Li_2O$ | 14.8 | 16.1 |
| $ZrO_2$ | 4.6 | 6.0 |
| $TiO_2$ | 0.6 | 2.4 |
| $P_2O_5$ | 2.5 | 3.0 |
| SnO | 0.0 | 0.2 |
| $Er_2O_3$ | 0.1 | 1.5 |
| $V_2O_5$ | 0.0 | 0.5 |
| $GeO_2$ | 0.9 | 7.8 |
| $Ta_2O_5$ | 0.0 | 2.3 |
| $Sm_2O_3$ | 1.8 | 5.7 |
| $Pr_2O_3$ | 0.0 | 0.9 |
| $Eu_2O_3$ | 0.0 | 1.3 |
| $Y_2O_3$ | 0.0 | 4.9 |
| $Nb_2O_5$ | 0.0 | 0.5 |

One preferred example of this material has the following specific composition:

TABLE 5

Preferred Composition

| Component | Weight % |
|---|---|
| $SiO_2$ | 55.74 |
| $Al_2O_3$ | 4.15 |
| $K_2O$ | 4.48 |
| CaO | 0.95 |
| $B_2O_3$ | 1.60 |
| MgO | 0.23 |
| Fluorine | 0.50 |
| $Li_2O$ | 16.01 |
| $ZrO_2$ | 4.76 |
| $TiO_2$ | 0.80 |
| $P_2O_5$ | 2.56 |
| $GeO_2$ | 0.91 |
| Coloring oxides | 7.32 |

Having thus disclosed a number of embodiments of the formulation of the present invention, including a preferred range of components, a preferred formula thereof and a preferred fabrication process, those having skill in the relevant arts will now perceive various modifications and additions. Therefore, the scope hereof is to be limited only by the appended claims and their equivalents.

I claim:

1. A lithium silicate dental glass ceramic article comprising a stable lithium silicate phase as a main crystalline phase and having a silicon dioxide and lithium oxide molar ratio content ($SiO_2/Li_2O$) of between 1.8 and 1.9, and further comprising germanium dioxide ($GeO_2$).

2. The lithium silicate dental glass ceramic article of claim 1 converted to a dental appliance restoration where only lithium silicate is formed as said main crystalline phase and there is no lithium disilicate crystalline phase.

3. The lithium silicate dental glass ceramic article of claim 1 further comprising at least one of $K_2O$; $Al_2O_3$; $ZrO_2$, and $Sm_2O_3$.

4. The lithium silicate dental glass ceramic article of claim 1 further comprising at least one of $P_2O_5$, $Pr_2O_3$, $TiO_2$, $Eu_2O_3$, $Er_2O_3$, and $V_2O_5$.

5. The lithium silicate dental glass ceramic article of claim 1 having a concentration of $GeO_2$ that is 1% to 9% by weight.

6. The lithium silicate dental glass ceramic article of claim 1 having a concentration of $SiO_2$ that is between 53% to 59% by weight.

7. The lithium silicate dental glass ceramic article of claim 1 having a concentration of $Li_2O$ that is between 14% to 19% by weight.

* * * * *